United States Patent
Sonis

(10) Patent No.: US 6,663,850 B2
(45) Date of Patent: Dec. 16, 2003

(54) INHIBITION OF CERAMIDE FOR THE PREVENTION AND TREATMENT OF ORAL MUCOSITIS INDUCED BY ANTINEOPLASTIC DRUGS OR RADIATION

(75) Inventor: Stephen T. Sonis, Wayland, MA (US)

(73) Assignee: Mucosal Therapeutics, LLC, Wellesley, MA (US)

( * ) Notice: Subject to any disclaimer, the term of this patent is extended or adjusted under 35 U.S.C. 154(b) by 0 days.

(21) Appl. No.: 10/062,701

(22) Filed: Jan. 31, 2002

(65) Prior Publication Data

US 2002/0071814 A1 Jun. 13, 2002

Related U.S. Application Data

(63) Continuation of application No. 09/801,435, filed on Mar. 7, 2001.
(60) Provisional application No. 60/187,533, filed on Mar. 7, 2000.

(51) Int. Cl.[7] .................. A61K 7/16; A61K 31/335; A61K 31/35
(52) U.S. Cl. .................. 424/49; 514/452; 514/456
(58) Field of Search .................. 514/428, 452, 514/456; 424/49–58

(56) References Cited

U.S. PATENT DOCUMENTS

| | | | | |
|---|---|---|---|---|
| 5,438,075 A | | 8/1995 | Skubitz et al. .............. 514/563 |
| 5,723,114 A | * | 3/1998 | Elias et al. | |
| 5,885,565 A | * | 3/1999 | Elias et al. | |
| 5,885,786 A | * | 3/1999 | Cabot | |
| 5,912,265 A | * | 6/1999 | Bombardelli et al. ....... 514/452 |
| 5,916,911 A | * | 6/1999 | Shayman et al. | |
| 5,945,442 A | * | 8/1999 | Shayman et al. | |
| 5,952,370 A | * | 9/1999 | Shayman et al. | |
| 5,962,424 A | * | 10/1999 | Hallahan et al. | |
| 6,010,691 A | * | 1/2000 | Elias et al. | |
| 6,040,332 A | * | 3/2000 | Shayman et al. | |
| 6,040,346 A | * | 3/2000 | Moretti | |
| 6,051,598 A | * | 4/2000 | Shayman et al. | |
| 6,090,565 A | * | 7/2000 | Cabot et al. | |
| 6,114,385 A | * | 9/2000 | Moretti | |
| 6,133,416 A | * | 10/2000 | Wilson et al. | |
| 6,143,785 A | * | 11/2000 | Cavazza | |
| 6,166,077 A | * | 12/2000 | De Simone | |
| 6,169,038 B1 | | 1/2001 | Hirano et al. .............. 514/184 |
| 6,190,894 B1 | * | 2/2001 | Elias et al. | |
| 6,217,898 B1 | * | 4/2001 | Cavazza et al. | |
| 6,218,369 B1 | * | 4/2001 | Bombardelli et al. ....... 514/452 |
| 6,245,800 B1 | * | 6/2001 | Arduini et al. | |

FOREIGN PATENT DOCUMENTS

| | | | | |
|---|---|---|---|---|
| WO | 96/37209 | * | 11/1996 | .......... A61K/35/78 |
| WO | 99 45 910 | * | 9/1999 | |

OTHER PUBLICATIONS

Abstract of Sonis VII Leukemia 13(6): 831–834, 1999.*
Abstract of Sonis VI Oral Oncol. 34(1): 39–43, 1998.*
Abstract of Sonis V Cytokine 9(8): 605–612, 1997.*
Abstract of Sonis IV Oral Oncol. 33(1): 47–54, 1997.*
Abstract of Sonis III Export Opin. Invest. Drugs 51(9): 1155–1162, 1996.*
Abstract of Sonis et al II Eur. J. Cancer B Oral Oncol. 31B(4): 261–266, 1997.*
Abstract of Sonis et al I Cancer Res. 54(5): 1135–8, 1994.*

* cited by examiner

Primary Examiner—Shep K. Rose
(74) Attorney, Agent, or Firm—Clark & Elbing, LLP

(57) ABSTRACT

Intervention for oral mucosal injury secondary to chemotherapy or radiation based on the inhibition in the synthesis of ceramide, blockage of its activity, or its digestion.

6 Claims, No Drawings

INHIBITION OF CERAMIDE FOR THE PREVENTION AND TREATMENT OF ORAL MUCOSITIS INDUCED BY ANTINEOPLASTIC DRUGS OR RADIATION

CROSS REFERENCE TO RELATED APPLICATIONS

This application is a continuation of and claims priority from U.S. patent application Ser. No. 09/801,435, filed Mar. 7, 2001, which claims benefit from U.S. Provisional Application No. 60/187,533, filed Mar. 7, 2000.

BACKGROUND OF THE INVENTION

Oral mucositis is a common, bothersome and dose-limiting side effect of many forms of cancer chemotherapy. The lesions that result cause inflammatory and ulcerative changes that result in pain and loss of function. Consequently, patients with mucositis have difficulty eating and require pain medication. Since the frequency and severity of mucositis are related to the choice and dose of the drug being used, oncologists may shy away from optimum agents and doses in order to avoid this side effect. In addition, patients who receive myeloablative therapy are at increased risk of local and systemic infection. Since the mouth is normally rich in microorganisms, the loss of mucosal integrity which accompanies mucositis at a time when patients' systemic defenses are compromised, results in the oral cavity being a major source of invading bacteria. In fact, the mouth is the most identifiable source of systemic bacteria in granulocytopenic cancer patients.

Patients who receive radiation therapy for tumors of the head and neck are also at high risk for oral mucositis. The frequency and severity of mucosal injury is a function of the total dose and schedule of radiation. Increasing the rate of radiation exposure results in a higher incidence of mucositis. While the current trend of using concomitant chemotherapy with radiation results in a better tumor outcome than radiation alone, these protocols are exceedingly stomatotoxic. Mucositis is often of such severity as to necessitate a break in treatment to allow the tissue to recover. Such an interruption in therapy reduces the overall anti-tumor effect of the radiation.

Historically mucositis was viewed as a process that was mediated by epithelial damage. It was believed that the non-specific toxic effects of chemotherapy or radiation resulted in DNA damage to the rapidly dividing cells of the oral basal epithelium. This resulted in cell death, atrophic changes of the mucosa, and ultimately, ulceration. However, four lines of observations suggested a biologic complexity that extended beyond an epithelial etiology. First, electron microscopic observations demonstrated that early damage was seen in both the endothelium and connective tissue underlying the epithelium and these changes preceded any noted in the epithelium. Second, administration of pleotropic cytokines which attenuated levels of the pro-inflammatory cytokines, IL-1β and TNF-α, resulted in a reduction of mucositis in experimental models. Third, high levels of the same pro-inflammatory cytokines were noted in the peripheral blood of patients with non-hematologic toxicities associated with cancer chemotherapy. And fourth, alteration of the local oral environment, particularly the bacterial load and saliva, modified the course of mucositis.

SUMMARY OF THE INVENTION

I believe that cells in the endothelium, connective and basal epithelium undergo apoptosis or cell death as mucositis progresses. While there are a number of mediators which influence this outcome, I posit that the sphingolipid messenger ceramide is a major molecular driver of cell death. Of particular relevance in this patient population is the fact that ceramide may be generated in one of two ways; first, from sphingomyelin by activation of either neutral or acidic sphingomylinase; or second from dihydrosphosine following activation of ceramide synthase. TNF-α, already known to play a significant role in mucositis development, actives both the acidic and neutral forms of sphingomylinase. Radiation may cause ceramide production by activation of the acidic form. Further, a number of chemotherapeutic drugs are known activators of ceramide synthase.

I propose an intervention for oral mucosal injury secondary to chemotherapy or radiation based on the inhibition of the synthesis of ceramide, blockage of its activity or by its digestion. Using a rinse and swish technique, suspensions of the drug can be used by patients immediately prior to, and continuing throughout the course of their active treatment. Topical pastes and gels can also be used. Among the possible agents are: Silymarin, a polyphenolic flavonoid derived from milk thistle, which blocks ceramide activity; 1-phenyl-2-decanoylaminon-3-morpholino-1-propanol and 1-phenyl-2-hexadecanoylaminon-3-pyrrolidino-1-propanol, both of which are inhibitors of glucosylceramide synthase; Scyphostatin, an inhibitor of neutral magnesium-dependent sphingomylinase; L-carnitine, an inhibitor of ceramide production; glutathione; and human milk bile salt-stimulated lipase, which digests ceramide.

DETAILED DESCRIPTION

The therapeutic compositions of the invention are preferably administered to human patients to prevent or treat mucositis in the form of an oral rinse, as a topical paste, or as a gel. When used to help in the prevention of mucositis, administration of the compositions preferably will precede a given treatment with anti-neoplastic therapy by 1–2 days. Daily treatment can continue during the course of anti-neoplastic treatment.

The concentrations of the therapeutic agents used in the compositions of the invention will vary depending on which compound is being used, and can be determined routinely for each compound using known methods. The pharmaceutically acceptable carrier vehicles (liquids, gels, or pastes) are all well known as vehicles for other oral/topical therapeutic compositions.

The active agents of the invention can be combined in the therapeutic compositions with other active agents, including anti-inflammatory agents such as ibuprofen, antimicrobial agents such as tetracycline, and analgesics such as lidocaine.

Preferred compositions are liquid suspensions, which can be rinsed and swished in the patient/s mouth, and gargled as well to ensure exposure of the active agent to the oropharynx. Preferably, this regimen is carried out daily over a fourteen day period to provide coverage through the first three phases of mucositis development.

Treatment according to the invention is particularly important in patients who received multiple cycles of chemotherapy, e.g., patients suffering from colorectal cancer, who receive monthly cycles of chemotherapy. These patients are at particular risk for developing mucositis. Patients in this group begin dosing with a therapeutic composition of the invention two hours prior to administration of chemotherapy, and then they continue topical application of the medication every four hours, while awake, for at least the next the 48 hours. This regimen is repeated for each dosing cycle.

What is claimed:

1. A method of treating mucositis in a human patient in need thereof, said method comprising diagnosing said patient with mucositis and administering to said patient an effective amount of a therapeutic composition comprising a compound that either inhibits the synthesis of ceramide, blocks the activity of ceramide, or degrades ceramide.

2. The method of claim 1, wherein said therapeutic composition is administered in the form of an oral rinse, a topical paste, or a gel.

3. The method of claim 1, wherein said compound is selected from the group consisting of silymarin, 1-phenyl-2-decanoylaminon-3-morpholino-1-propanol, 1-phenyl-2-hexadecanoylaminon-3-pyrrolidino-1-propanol, Scyphostatin, L-carnitine, glutathione, and human milk bile salt-stimulated lipase.

4. The method of claim 1, wherein said mucositis is oral mucositis.

5. The method of claim 1, wherein said patient is undergoing radiation for the treatment of cancer.

6. The method of claim 1, wherein said patient is undergoing chemotherapy.

\* \* \* \* \*